United States Patent [19]
Wang et al.

[11] Patent Number: 4,568,644
[45] Date of Patent: Feb. 4, 1986

[54] FERMENTATION METHOD PRODUCING ETHANOL

[75] Inventors: Daniel I. C. Wang, Belmont, Mass.; Rajen Dalal, Chicago, Ill.

[73] Assignee: Massachusetts Institute of Technology, Cambridge, Mass.

[21] Appl. No.: 640,247

[22] Filed: Aug. 13, 1984

Related U.S. Application Data

[63] Continuation of Ser. No. 329,448, Dec. 10, 1981, abandoned.

[51] Int. Cl.$^4$ .......................... C12P 7/06; C12R 1/145
[52] U.S. Cl. ................................. 435/161; 435/172.1; 435/253; 435/842
[58] Field of Search ............... 435/842, 161, 163, 165, 435/172.1, 253

[56] References Cited

U.S. PATENT DOCUMENTS 4,211,846  7/1980  Lafferty ............................. 435/146
4,400,470  8/1983  Zeikos et al. ....................... 435/162

OTHER PUBLICATIONS

"Advances in Biotechnology", vol. II, #18, Avgerinos et al. p. 119–124, Jul. 1980.

Primary Examiner—S. Leon Bashore
Assistant Examiner—K. M. Hastings
Attorney, Agent, or Firm—Paul J. Cook

[57] ABSTRACT

Ethanol is the major end product of an anaerobic, thermophilic fermentation process using a mutant strain of bacterium *Clostridium thermosaccharolyticum*. This organism is capable of converting hexose and pentose carbohydrates to ethanol, acetic and lactic acids. Mutants of *Clostridium thermosaccharolyticum* are capable of converting these substrates to ethanol in exceptionally high yield and with increased productivity. Both the mutant organism and the technique for its isolation are provided.

7 Claims, No Drawings

FERMENTATION METHOD PRODUCING ETHANOL

The Government has rights in this invention pursuant to D.O.E. Subcontract Number XR-9-8109-1, (S.E.R.I. Prime Contract Number EG-77-C-01-4042), awarded by the U.S. Department of Energy.

This application is a continuation of application Ser. No. 329,448, filed Dec. 10, 1981, now abandoned.

BACKGROUND OF THE INVENTION

This invention relates to a new bacterial strain and to a fermentation process for producing ethanol utilizing the bacterial strain.

Presently there are a variety of fermentation processes for producing ethanol from different feedstock materials and having different organisms. Corn stover presently is an abundant source of cellulosic material which consists of the leaves and stalks of the plant remaining after the removal of the cob. In the United States, in 1979, $6.4 \times 10^9$ bushels of corn were produced. The amount of corn stover associated with this corn starch production and at a theoretical yield utilizing 100% of the available carbohydrate in the corn stover, can represent a quantity of biomass capable of producing 14,000,000,000 gallons of ethanol; roughly 10% of the domestic gasoline consumption in 1979. Presently there are a number of problems to the realization of this potential. When a yeast such as *Saccharomyces cerevisiae* is used for ethanol production, only the hexose portion of the biomass (approximately only 55% of total biomass) can be fermented. In addition, these hexose sugar polymers must be hydrolyzed prior to fermentation. Although this has previously been accomplished by high temperature and chemical pretreatment, or more recently, by enzymatic hydrolysis following addition of cellulases obtained from the fungus *Trichoderma reeseii*, it is accompanied by the serious drawbacks of high cost as well as low yields of fermentable sugars. As an alternative to these multi-stage methods involving prehydrolysis of cellulose, it has been proposed to ferment insoluble cellulosics to ethanol with the thermophilic, cellulolytic, anaerobe, *Clostridium thermocellum*. Both the cellulose and hemicellulose fraction, making up about 40 and 30% respectively of the biomass substrate, such as corn stover, are hydrolyzed. The hexose is produced or metabolized predominantly to a mixture to ethanol, acetate and lactate.

However, this organism, like yeast, cannot ferment the pentoses cleaved from the hemicellulose. In order to increase the economic potential of this biomass feedstock, it is desirable to provide a means for metabolizing these sugars as well. It is known that the termophilic anaerobe *Clostridium thermosaccharolyticum* can metabolize hexose and pentose carbohydrates to produce ethanol. However, it is also known that this bacterium simultaneously produces lactic and acetic acids in amounts approximately equal to the ethanol produced. This is highly undesirable since the majority of the input feedstock carbohydrates utilized in the fermentation processes is metabolized to the undesirable co-products, acetic acid and lactic acid.

Accordingly, it would be highly desirable to provide a means for selectively forming ethanol from a cellulosic source while minimizing the production of the undesirable co-products, acetic and lactic acids. Furthermore, it would be desirable to provide a means for metabolism of pentoses to produce ethanol.

SUMMARY OF THE INVENTION

In accordance with this invention, a new bacterial strain is provided. It is a mutant of the thermophilic anaerobe *Clostridium thermosaccharolyticum*, which, unlike the parent strain, will effect the fermentation of hexose and pentose carbohydrates to selectively produce high yield and concentration of ethanol while simultaneously producing diminished concentrations of undesirable products such that the ratio of ethanol to acetic acid is at least about 8:1. The process for isolation of this mutant is based upon the discovery that mutants unable to grow on pyruvate as the sole carbon source are likely to have a diminished capability to produce acetic acid and an enhanced capability to produce ethanol. This mutant strain can be utilized either alone to ferment pentose and hexose carbohydrates or in combination with bacteria that convert insoluble carbohydrates such as cellulose or hemicellulose to soluble sugars or with enzymes which can accomplish this saccharification.

DESCRIPTION OF SPECIFIC EMBODIMENTS

The bacterial strain utilized in the present invention is produced by mutation of *Clostridium thermosaccharolyticum* with a mutagenic agent such as ultraviolet light, gamma radiation, nitrosoguanidine, ethyl methanesulfonate or other known agents. The novel microorganisms of this invention are strains of *Clostridium thermosaccharolyticum* which exhibit the following characteristics:

Unlike presently available strains of *Clostridium thermosaccharolyticum* which ferment hexose and pentose carbohydrates to form approximately equal concentrations of ethanol, acetic acid and lactic acid, the mutant strain of this invention produces ethanol at an enhanced gram ratio of ethanol to lactic acid of at least about 12:1. The mutant strain, also unlike presently available strains, exhibits increased tolerance to the desired end product, ethanol, and can accumulate ethanol to significantly higher levels. The yield of ethanol produced from xylose is also significantly improved.

A mutant strain utilized in the present invention has been assigned ATCC No. 31960 by the American Type Culture Collection, 12301 Parklawn Drive, Rockville, Md. 20852.

The low acetic acid producing mutant strain of this invention is isolated by a procedure based upon the fact that strains which produce acetic acid also grow on pyruvate, while mutant strains that effect the conversion of cellulosic materials primarily to ethanol do not grow on pyruvate. Strains capable of utilizing pyruvate for growth as the sole carbon source, produce ATP by acetate kinase catalyzed reactions and hence acetic acid as the end product. Therefore, among mutants unable to utilize pyruvate for growth should be mutants which are deficient in acetate kinase and therefore unable to synthesize ATP. Such a mutant would produce less or no acetic acid.

In the procedure, the bacterium *Clostridium thermosaccharolyticum*, ATCC No. 31925, is exposed to a mutagen for a sufficient period of time to effect the formation of mutants. The mutagenized cultures then are incubated in liquid CM4 growth medium containing 5–15 g/l pyruvate. The mutant strains which produce ethanol do not grow in this medium, whereas mutant strains which produce significant quantities of acetic acid do grow on this medium. The high ethanol and low acetic acid producing cultures then are enriched with penicillin. This enrichment results in the killing of the growing strains, but not of the strains that do not grow on pyruvate. The nongrowing strains survive and are isolated. Isolation of mutants is accomplished by differential media plating on agar containing 1.5% pyruvate CM4 and 0.5 g/l yeast extract. Plating of the mutagenized and enriched population of *C. thermosaccharolyticum* on this media results in the formation of large and small colonies. The larger ones generally ferment pyruvate and still produce acetic acid. However, the smaller colonies generally do not ferment pyruvate and may produce ethanol in higher yield. These promising colonies are picked for further evaluation and subsequent use in a fermentation process utilizing cellulosic materials.

In accordance with this invention, the mutant bacterial strain is utilized to effect fermentation of hexose and pentose carbohydrates. These carbohydrates may be obtained by the addition of cellulases, xylanases to biomass or by co-culture with a cellulolytic organism such as *C. thermocellum* on various biomass substrates. A typical cellulosic material useful in the present invention is obtained from ground corn stover (stalk and cob) and straws such as wheat and rice straw. (A preferred feedstock is described in co-pending application, Ser. No. 292,314, entitled "Selective Solvent Extraction of Cellulosic Material" filed in the names of Daniel I. C. Wang and George C. Avgerinos, filed Aug. 12, 1981, and which is incorporated herein by reference. These feedstocks derived from corn stover have a weight ratio of pentosan to lignin of at least about 5:1 and a weight ratio of cellulose and hemicellulose to lignin of at least about 10:1.) Fermentation can be conducted as either a batch or a continuous process. In the batch process, the bacterium is mixed with an aqueous suspension of the cellulosic material, generally at a pH between about 6 and about 7, and under an atmosphere which excludes oxygen. The bacterium and substrate are maintained at a temperature between about 55 and about 65° C., preferably between about 59° and about 61° C.

This fermentation may also be operated in a continuous mode. In such a process, an aqueous suspension of the cellulosic material or soluble sugars are pumped into the fermentor at a constant flow rate and the culture broth is continuously removed in order to maintain a constant volume in the fermentation vessel. At steady state, the growth rate of the cells is equal to the dilution rate: the incoming flow rate divided by the total volume. One advantage of continuous fermentation is that the productivity is generally much higher than in the case of batch fermentation.

Ethanol is recovered from the fermentation broth by distillation.

The following examples illustrate the present invention and are not intended to limit the same.

Example I

This example illustrates the formation of a mutant of *Clostridium thermosaccharolyticum* useful in the process of this invention. The selection of mutant is based upon the fact that mutants which produce significant concentrations of acetic acid can be grown on pyruvate, while mutants which primarily produce ethanol do not. A growth medium comprising 1-1.5% sodium pyruvate (filter sterilized) and CM-4 medium was utilized for the growth of the bacterial culture. Exponentially growing cells in a Hungate tube were grown in a growth medium comprising CM-4 xylose medium to an optical density $=0.4$–$0.6$ measured at 660 nm. The growing cells were then exposed to 150 krads of gamma-irradiation from a Cobalt 60 source. Cells from each tube are placed individually into 5 ml of 1% yeast extract and 1% peptone supplemented CM-4 medium in the Hungate tube and recovered.

| CM4 Media | |
|---|---|
| | g |
| $KH_2PO_4$ | 1.5 |
| $K_2HPO_4$ | 2.9 |
| Sodium thioglycollate | 0.5 |
| Resazurin | $2 \times 10^{-6}$ (0.2 ml of a 1.0 solution) |
| $(NH_4)_2SO_4$ | 1.3 |
| $MgCl_2$ | 0.75 |
| NaCl | 1.0 |
| $CaCl_2$ | 0.0132 |
| $PeSO_4$ | $1.25 \times 10^{-6}$ (0.1 ml of a 1.25% solution) |
| Carbon Source | 6.0 |
| $H_2O$ | 1000 |

The resultant composition is then innoculated in 5 ml of 1% CM-4 xylose and grown. A 10% innoculum was transferred to 5 ml of 1.5% pyruvate CM-4 (defined medium) or 1.5% pyruvate CM-4 medium with only 0.5 g/l yeast extract, allowing 1 doubling for xylose carryover exhaustion. 25 units/ml of penicillin then was added to each sample which was then observed until optical density at 660 nm decreased, which took approximately 10 hours. Each sample was then agitated, centrifuged and washed with reduced 30 mM $PO_4$, at a pH of 7.0. The resultant cells then were transferred to 2 ml of CM-4 xylose 1% solution and grown after resuspension. The final 4 steps set forth above were repeated 4 times, the final round being processed with cycloserine instead of penicillin or ampicillin. The samples containing live cells were then recovered and plated on differential CM-4 agar medium containing 15 g/l pyruvate and only 0.5 g/l yeast extract. When 50–100 colonies per plate are grown on CM 4 +14 g/l pyruvate, the colonies are uniformly 1.5 mm in diameter. With this information it was anticipated that the pyruvate negative but xylose positive colonies would remain relatively small (less than 0.5 mm) utilizing only the yeast extract, whereas all the pyruvate positive cells would grow larger than 1 mm. Therefore, from among the small colonies could be found low acetic acid producers.

In conclusion, the results demonstrate that small colonies are enriched during penicillin treatment of cells growing on pyruvate and that among small colonies, the frequency of mutants isolated with ethanol/acetic acid ratio greater than 8 was greater than 10 fold. The small colonies obtained by this screening method and having this production ratio occurred in a 1 in 175 frequency. Thus, the use of pyruvate for mutant screening and in conjunction with penicillin for enrichment provides a specific selection method as well as a method for increasing the frequency of finding acetic acid non-producers. All of the mutants produced ethanol selectively at a ratio of ethanol to acetic acid of at least 8, but some synthesized more ethanol than others. In other words, different mutational events may effect the same end result; all are selective producers of ethanol, but some are more efficient than others. The highest producing mutant of those tested was designated *Clostridium thermosaccharolyticum* ATCC No. 31960.

Example II

In order to evaluate the fermentation performance of 5 isolated mutants, isolate *Clostridium thermosaccharolyticum* ATCC No. 31960 was chosen on the basis of its ethanol formation on CM-4 cylose in Hungate tubes. The g ethanol/g acetate product ratio of this organism was 12:5 in Hungate tubes.

4 liters of media were fermented in a 7 liter fermentor under pH control at pH 6.6. Xylose concentration was maintained between 5 and 15 g/l by periodic batch feeding. Additional 10 g/l yeast extract was provided during the fermentation.

During the growth phase (0–40 hours), cell mass increased rapidly (specific growth rate, $\mu = 0.10$–$0.15$ $hr^{-1}$) following which cell mass decreased. When cell mass stopped increasing at 40 h, further addition of nutrients did not alter the trend. Ethanol accumulation also ceased with cell growth. At the termination of the fermentation, about 45 g/l ethanol accumulated from about 105 g/l xylose, a yield of about 0.43. Furthermore, acetic acid accumulation does not exceed 4 g/l, thereby providing an effective g ethanol/g acetic acid ratio of 11:1.

In conclusion, the mutant isolated by the previously described method has been shown to possess the sought characteristics of producing a higher ethanol concentration at a greater yield from xylose and at a significantly improved ethanol to acetate ratio.

We claim:

1. A mutant strain of *Clostridium thermosaccharolyticum* which is unable to utilize pyruvate as a source of carbon and ferments hexose and pentose carbohydrates to produce ethanol and acetic acid at a gram ratio of at least about 8:1.

2. A biologically pure bacterial strain comprising *Clostridium thermosaccharolyticum* ATCC 31960.

3. A process for preparing and isolating a mutant strain of *Clostridium thermosaccharolyticum*, said mutant strain being able to ferment hexose and pentose carbohydrates to produce ethanol and acetic acid in gram ratios of at least about 8:1, said process comprising the steps of:

exposing *Clostridium thermosaccharolyticum* cells to a mutagenic agent sufficient to effect mutation of said cells;

culturing said mutated cells in a growth medium containing minimal carbon sources and pyruvate for a predetermined time period;

enriching said growth medium with at least one antibiotic, said antibiotic killing the actively growing cells in said medium without substantially affecting the non-actively growing cells; and isolating a mutant *Clostridium thermosaccharolyticum* strain from said non-actively growing cells via the inability to utilize pyruvate as a carbon source.

4. The process as recited in claim 3 wherein said antibiotic is penicillin.

5. A process for producing ethanol comprising the step of:

growing a mutant strain of *Clostridium thermosaccharolyticum* in growth medium containing at least one carbohydrate selected from the group consisting of hexose carbohydrates, pentose carbohydrates, and mixtures of hexose and pentose carbohydrates, said mutant strain being unable to utilize pyruvate as a source of carbon and fermenting hexose and pentose carbohydrates to ethanol and acetic acid at a gram ratio of at least about 8:1.

6. The process as recited in claim 5 wherein the growth medium and the carbohydrate are continuously added to said mutant strain in a culture vessel and said ethanol is removed from said culture vessel.

7. The process as recited in claim 5 wherein growth medium and carbohydrate are continuously added to *Clostridium thermosaccharolyticum* ATCC Number 31960 in a culture vessel and said ethanol is removed from said culture vessel.

* * * * *